United States Patent [19]

Ebbesen

[11] Patent Number: 4,778,677
[45] Date of Patent: Oct. 18, 1988

[54] METHOD FOR TREATMENT OF NICOTINE CRAVING

[76] Inventor: Gerald K. Ebbesen, Dover Rd., South Newfane, Vt. 05351

[21] Appl. No.: 523,295

[22] Filed: Aug. 15, 1983

Related U.S. Application Data

[63] Continuation of Ser. No. 281,866, Jul. 9, 1981, abandoned.

[51] Int. Cl.$^4$ .................. A61K 33/42; A61K 33/14; A61K 31/70; A61K 31/52
[52] U.S. Cl. ................................ 424/128; 424/153; 514/23; 514/264; 514/813
[58] Field of Search ............... 424/153, 128, 253, 125, 424/180; 514/264, 23

[56] References Cited

U.S. PATENT DOCUMENTS

| 1,229,656 | 6/1917 | Rosewater | 424/253 |
| 2,705,695 | 4/1955 | Rapp | 424/128 |
| 3,094,531 | 6/1963 | Klosa | 260/256 |
| 3,337,404 | 8/1967 | Polli | 167/57 |
| 3,356,570 | 12/1967 | Butcher | 167/58 |
| 3,740,433 | 6/1973 | Clody | 424/253 |
| 3,864,489 | 2/1975 | Biscardi | 424/253 |

OTHER PUBLICATIONS

Wright, et al.-Journal A.M.A., vol. 109, No. 9, 649–654.
*The Merck Manual,* 1977, Merck & Co., Inc., Rahway, N.J., pp. 650–652.
Merck Index, 9th Edition, p. 1625.

*Primary Examiner*—Frederick E. Waddell

[57] ABSTRACT

A method for the treatment of the craving for nicotine in nicotine withdrawal syndrome comprising administering to the patient a composition including glucose or a sugar convertable to glucose in the body of the patient, potassium in ionic form (K+) or a potassium compound capable of dissociating in vivo to release potassium ions, and caffeine or a xanthine equivalent to caffeine in its capacity to elevate the metabolic rate, the glucose and potassium being present in an amount to quickly restore the levels of blood glucose and potassium in the patient to that which his body has become accustomed as a result of repeated nicotine stimulation, caffeine being present in an amount to stimulate metabolism and mental alertness to which his central nervous system has become accustomed by repeated nicotine stimulation.

11 Claims, No Drawings

METHOD FOR TREATMENT OF NICOTINE CRAVING

This application is a continuation of application Ser. No. 281,866, filed July 9, 1981, now abandoned.

BACKGROUND OF THE INVENTION

This invention relates to the oral administration of a composition of matter having the therapeutic property of alleviating the craving for nicotine that accompanies the nicotine withdrawal syndrome.

Therapeutic efforts to break the tobacco smoking habit either through psychological approaches or through the use of various filters or cigarette substitutes have met with varying degrees of sucess.

It is generally recognized that bio-feedback from altered physical states can exert an influence on the psyche. The altered physical state induced by tobacco influences the psyche to an extent sufficient to account for a significant measure of its habit forming potential. This physiological component of the cigarette habit can be treated by oral therapy.

It is common knowledge that smokers who quit the habit tend to gain weight. Usually they crave sweets and in satisfying that craving they gain weight. Physicians cite cases of smokers who have broken the habit only to return to smoking owing to undesirable weight gain.

At the University of Wisconsin students were asked to place a thin wire through a small opening in a copper plate without touching the sides of the opening. An electric counter recorded the number of times contact was made with the sides of the opening. Smokers scored 60% poorer than nonsmokers. This strongly suggests that tremors were present in a greater degree in the smokers than in nonsmokers.

A successful oral therapeutic approach to tabacco withdrawal symptoms must therefore alleviate the two physical effects of the tobacco habit cited above, i.e., weight gain and tremors.

Tobacco smoke produces changes almost identical with that produced by adrenaline, including a rise in blood sugar. Nicotine, through its effect on the adrenals, increases the metabolic rate. Tobacco smoke also causes increases of oxygen consumption by an average of 30%. It is known that the potassium content of the blood rises and falls in parallel with the sugar content of the blood. This potassium and glucose tide accounts for some of the habit forming potential of nicotine addiction.

Some of the euphoria accompanying tobacco usage is due to the rise in both metabolic rate and blood sugar. Adrenaline secretion is increased by nicotine stimulation. Since adrenaline is a potent inhibitor of insulin, it not only provides glucose to the circulation, but also, because it decreases glucose uptake by peripheral tissues, glucose is preferentially preserved for utilization by the brain. This accounts for the improved capacity for mental concentration asserted by tobacco users.

Initially, nicotine stimulates the adrenal medulla and epinephrine is thereby discharged. This initial phase is transient and is followed by a paralysis of the secretory process. The degree of hypoglycemia which follows the primary rise in blood sugar may amount to a drop to 50-70 mgs/100 ml. The glycogen stores of the brain and nerves are very small. Hence a minute-to-minute supply of glucose is particularly important to the nervous system.

The dependence of various tissues upon circulating blood glucose varies widely. The central nervous system is perhaps most critically dependent, since glucose is the only nutrient that crosses the blood-brain barrier at a rate sufficient to sustain normal function. If the blood-glucose concentration falls abruptly, the earliest symptoms observed are referrable to the central nervous system.

The fall in blood sugar is accompanied by a fall in blood potassium. A low potassium blood level (hypokalemia) is associated with irritability, tremors, nervousness and electrocardiograph changes such as ST segment depression and T-wave inversion.

In tobacco withdrawal there are tremors, anxiety, nervousness, craving and irritability. EKGs taken on chronic smokers exhibit a decrease in amplitude or inversion of the T-wave.

I have discovered that the craving and habit forming aspect of tobacco withdrawal has a physiological component that is caused by the associated hypoglycemia and hypokalemia. It becomes apparent that the effects of nicotine stimulation produce an initial "lift" which is followed by a period of mild depression accompanied by bodily changes of the nature described above. Owing to the reciprocity existing between emotional experiences and physiological changes, the physiological changes noted above contribute, through bio-feedback, to the emotional dependence on the tobacco habit.

It is known that the elevation of the metabolic rate by as much as 25% can be achieved by the administration of caffeine. In addition, it is known that caffeine is also a powerful stimulant of the central nervous system. Its main action on the cortex is on psychic and sensory functions. It produces a clearer flow of thought, and motor activity is also improved.

DESCRIPTION OF THE PRIOR ART

U.S. Pat. No. 2,446,916 to Freedman, issued Aug. 10, 1948, is directed to a therapeutic composition described as useful only for lowering blood pressure or producing a diuretic effect, comprising, inter alia, dextrose, caffeine and potassium nicotinate. Moreover, the amount of dextrose in this composition, as obtained by stoichiometric calculation, is far too low (0.35 grams) for it to have any substantial effect in elevating blood sugar.

U.S. Pat. No. 2,999,293 to Taff, issued Sept. 12, 1961, discloses a preparation containing bromides (not specifically potassium bromide), caffeine and a sweetening agent. No therapeutic use therefor of any kind is mentioned. Moreover, the amount of sugar employed therein is far too low for it to have any substantial effect in elevating blood sugar.

U.S. Pat. No. 3,105,792 to White, issued Oct. 1, 1963, discloses a therapeutic composition comprising, inter alia, potassium bromide, caffeine and a sweetening agent. There is no disclosure of employing this composition for the treatment of the symptoms of nicotine withdrawal syndrome.

U.S. Pat. No. 4,061,797 to Hannan, Jr. et al, issued Dec. 6, 1977, discloses in Example 6 a cola beverage formulation containing, inter alia, caffeine and orange juice. Orange juice, as is well known, contains both potassium ions and glucose, This patent teaches no therapeutic effect of any kind for the beverage it discloses.

SUMMARY OF THE INVENTION

It has now been discovered in accordance with the present invention that the deficiencies of previously proposed procedures for the treatment of withdrawal symptoms in tobacco smoking individuals can be eliminated. Through the provision of the method of the present invention, a tobacco smoking individual suffering from withdrawal symptoms can be treated without encountering the deficiencies and drawbacks of previous treatments by the oral administration of a composition containing (a) glucose or equivalent sugar, (b) potassium ions, and (c) caffeine or equivalent xanthines. The composition may be administered orally in the form of a liquid, gell, tablet, or as a powder. So far as is known from the published prior art, the composition of this invention has never been previously applied in the treatment of the symptoms of nicotine withdrawal syndrome.

The approach of the present invention is to provide glucose and potassium in such proportions as to raise the blood glucose and potassium to a level to which a smoker has become accustomed, and also to provide caffeine in such proportions to stimulate metabolism to the level to which the smoker has become accustomed, thereby to recreate the biochemical enviroment to which the smoker's body has become accustomed.

With respect to the foregoing, it appears to be pertinent to point out that the normal range of blood glucose in a nonsmoker is 80-120 mgs/100 ml. The normal range of blood potassium in a nonsmoker is 3.5-5.0 mEq/liter.

When a patient suffering from the symptoms of nicotine withdrawal syndrome is treated with glucose and potassium alone they cannot serve to increase the metabolic rate to the level to which a smoker has become accustomed so as to recreate the biochemical enviroment to which his body has become accustomed. The addition of caffeine to the glucose and potassium stimulates metabolism and enhances the speed of recovery from the symptoms of nicotine withdrawal syndrome, as well as the completeness of the recovdry. The stimulated metabolism enables the brain to absorb more oxygen and glucose. Additionally, caffeine suppresses insulin, thereby stimulating the brain.

DESCRIPTION OF PREFERRED EMBODIMENTS

Source of Glucose

The sugar should preferably be glucose. Before any sugar can be utilized by the body it must be broken down to glucose. However, if glucose is unavailable, sucrose (ordinary household sugar), fructose, invert sugar, maltose, lactose or galactose may be substituted.

Source of Potassium

Potassium in ionic form may be provided by any of the non-deleterious salts of potassium. Examples are as follows: acetate, citrate, carbonate, gluconate, pH balanced mono- and di-basic phosphate, and chloride. Although these are the preferred potassium salts, any potassium compound that will release potassium in ionic form without introducing any unwanted side effects may be substituted.

With respect to other potassium salts that have cations with medicinal properties, e.g., bromide, salicylate, iodide, nitrate, etc., it is pointed out that the use of these in significant quantities in the composition of the present invention may have some undesirable effects. This is due to the fact that the purpose of the composition of the present invention is to provide potassium ions quickly to the blood plasma.

Source of Caffeine

Examples of suitable sources of caffeine are as follows: pure caffeine, caffeine combined with acetate, citrate, benzoate, phosphate, sulfate or salicylate. Also suitable are any of the xanthine analogues that match caffeine's effectiveness as a central nervous system stimulant, including salts thereof that are compatible.

Source of Other Ingredients

Examples of suitable flavorings are as follows: spearmint, peppermint, saccharin, wintergreen, cinnamon, anise, fruit flavoring or any other flavorings that will mask the bitterness of caffeine and the saltiness of potassium salts.

Examples of preservatives are: sodium benzoate, sulfite salts, methylparaben and ascorbic acid.

Examples of diluents are as follows: water, carbonated beverage, fruit juices, milk and any other potable liquid in which the ingredients are soluble.

Examples of fillers are as follows: stearates, cellulose, methylcellulose, starch, gelatin, aluminum silicate, calcium phosphate, calcium sulfate, polyalkyleneglycols, and various gums, viz., tragacanth, acacia, arabic.

Examples of binders are as follows: gum tragacanth, gum arabic, Irish Moss extract, sodium algenates, colloidal magnesium, aluminum silicates, carboxymethylcellulose, vegetable oils and the included sugar (glucose).

The composition of the present invention may be dispensed in liquid form, as a tablet, as a gel, or as a powder. Examples of the liquid form are as follows. Any palatable liquid such as water, milk, carbonated beverage, or other potable liquid in which the ingredients are soluble.

Regardless of the exact form in which the composition of the present invention may be dispensed, the range of essential ingredients in a single dose is as follows, wherein a dose is defined as a single application comprised of one or more basic units, i.e., tablet, tablespoon, etc.

Sugar 2.0 to 5.0 grams
Elemental potassium 0.050 to 0.100 grams
Caffeine 0.030 to 0.060 grams.

EXAMPLE I (Liquid Formulation)

Glucose: 10.000 grams
Potassium gluconate: 0.600 grams
Caffeine: 0.100 grams
Citric acid: 0.100 grams
Preservative (Sodium benzoate): 0.075 grams
Flavoring (Lemon oil): To taste
Water: 30.000 ml.

Dosage: As a lower limit, the moderate smoker will take one tablespoon each hour, and a heavy smoker will take one-half tablespoon each one-half hour. As an upper limit, the moderate smoker will take two tablespoons each hour, and a heavy smoker will take one tablespoon each one-half hour.

EXAMPLE II

(Tablet Formulation)

Glucose: 2.500 grams
Potassium (in compound): 0.025 grams
Caffeine: 0.025 grams
Flavoring (Peppermint oil): To taste
Filler (Acacia): To desired consistency and frangibility.

Dosage: As a lower limit, the moderate smoker will take two tablets each hour, and a heavy smoker will take one tablet each one-half hour. As an upper limit, the moderate smoker will take four tablets each hour, and the heavy smoker will take two tablets each one-half hour.

The tablet size restricts the dose range. The larger tablets containing larter amounts of glucose will render them inconvenient for oral intake. Lesser amounts of glucose will make the tablets less effective. The other ingredients also have to be restricted in the lesser amounts.

EXAMPLE III

(Powder Formulation)

Glucose: 2.600 grams
Potassium gluconate: 0.150 grams
Caffeine: 0.025 grams
Citric acid: 0.025 grams
Flavoring (Lemon oil): To taste.

Dosage: As a lower limit, a moderate smoker will take two level teaspoons dissolved in water, or other liquid, each hour, and a heavy smoker will take one teaspoon dissolved in a liquid each one-half hour. As an upper limit, the above dosage is doubled.

EXAMPLE IV

(Gum Drops of Gel)

Glucose: 5.000 grams
Potassium gluconate: 0.585 grams
Caffeine citrate: 0.200 grams
Water: 6.500 ml.
Gelatine: 0.500 grams
Flavoring extract: 0.500 ml.

Dissolve the solid ingredients in the water while heating. Bring slowly to a boil, and boil for 10 minutes. Pour into a shallow pan and let cool for 12 hours. Cou into six one-ounce squares.

While I have described my presently preffered embodiments of my invention, it should be understood that the invention is not to be limited to the exact embodiments discussed herein. In view of my present teachings, further embodiments falling within the scope of the following claims will be apparent to those skilled in the art.

I claim:

1. A method of treating a patient subject to or suffering from the craving symptoms of nicotine withdrawal comprising administering to the patient a single dose of a composition containing:
   (a) glucose or a sugar convertible to glucose in the body of the patient;
   (b) potassium in ionic form (K+), or a potassium compound capable of dissociating in vivo to release potassium ions; and
   (c) caffeine or a xanthene equivalent to caffeine in the elevation of metabolic rate:
   the amounts of these ingredients which are incorporated in the single dose being effective to quickly restore to the levels to which a smoker is accustomed the blood glucose and potassium in the patient and also to stimulate the metabolism in the patient to the level to which a smoker is accustomed.

2. The process as recited in claim 1 in which component (a) is glucose.

3. A process as recited in claim 1 in which component (c) is caffeine.

4. A process as recited in claim 1 in which component (a) is glucose and component (c) is caffeine.

5. A process as recited in claim 1 in which component (a) is present in the range of 2 to 5 grams, component (b) is present in the range of 0.05 to 0.100 grams, and component (c) is present in the range of 0.03 to 0.06 grams, per dose.

6. A process as recited in claim 1 in which component (b) is potassium in ionic form (K+).

7. A process as recited in claim 4 wherein component (b) is potassium in ionic form (K+).

8. A process as recited in claim 5 in which component (a) is glucose.

9. A process as recited in claim 5 in which component (c) is caffeine.

10. A process as recited in claim 5 in which component (a) is glucose and component (c) is caffeine.

11. A process as claimed in claim 10 in which component (b) is potassium in ionic form (K+).